(12) United States Patent
Perera et al.

(10) Patent No.: US 11,214,791 B2
(45) Date of Patent: Jan. 4, 2022

(54) ENGINEERED FHA DOMAINS

(71) Applicant: Idea Orchard, LLC, City of Industry, CA (US)

(72) Inventors: Rajika Perera, Pasadena, CA (US); Michael Longo, Whittier, CA (US)

(73) Assignee: Idea Orchard, LLC

( * ) Notice: Subject to any disclaimer, the term of this patent is extended or adjusted under 35 U.S.C. 154(b) by 0 days.

(21) Appl. No.: 16/096,267

(22) PCT Filed: Apr. 25, 2017

(86) PCT No.: PCT/US2017/029484
§ 371 (c)(1),
(2) Date: Oct. 24, 2018

(87) PCT Pub. No.: WO2017/189624
PCT Pub. Date: Nov. 2, 2017

(65) Prior Publication Data
US 2019/0127730 A1    May 2, 2019

Related U.S. Application Data

(60) Provisional application No. 62/327,422, filed on Apr. 25, 2016.

(51) Int. Cl.
| C40B 40/10 | (2006.01) |
| C12N 15/10 | (2006.01) |
| C07K 14/47 | (2006.01) |

(52) U.S. Cl.
CPC .......... *C12N 15/1041* (2013.01); *C07K 14/47* (2013.01); *C12N 15/1027* (2013.01); *C40B 40/10* (2013.01)

(58) Field of Classification Search
None
See application file for complete search history.

(56) References Cited

U.S. PATENT DOCUMENTS

| 2009/0259026 A1* | 10/2009 | Tomlinson ............. C07K 16/18 |
| | | 530/387.3 |
| 2016/0090400 A1* | 3/2016 | Longo .................. C12N 15/102 |
| | | 530/350 |

* cited by examiner

*Primary Examiner* — Christian C Boesen
(74) *Attorney, Agent, or Firm* — Marshall A. Lerner; Kleinberg & Lerner, LLP.

(57) ABSTRACT

A binding agent to a target molecule, or method or kit where the binding agent is selected from a library where each variant has a circular permutation of the FHA domain where the rearrange does not substantially disrupt the FHA domain's beta-sheet scaffold or increase the stability of the beta-sheet scaffold. The randomized regions of the FHA domain include the endogenous binding interface the FHA domain, the region opposite of the endogenous binding interface, and the circular permutation region.

14 Claims, 6 Drawing Sheets
Specification includes a Sequence Listing.

FIG. 1A  2G1L
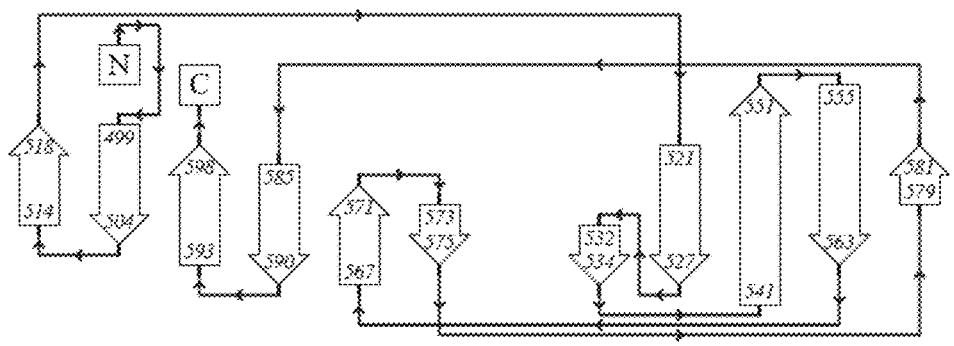
FIG. 1B  2G1L_M1
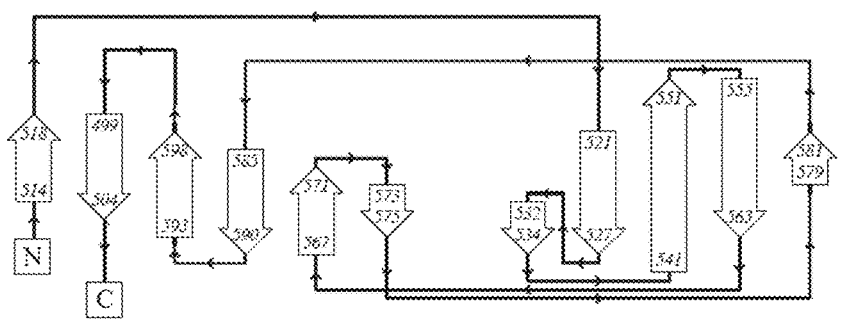
FIG. 1C  2G1L_M2
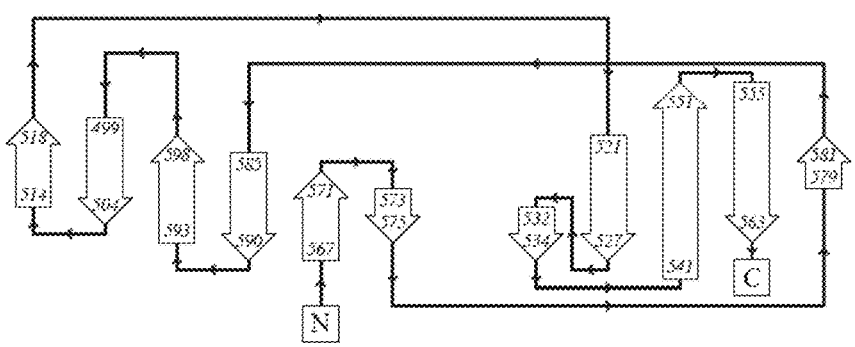
FIG. 1D  2G1L_M3
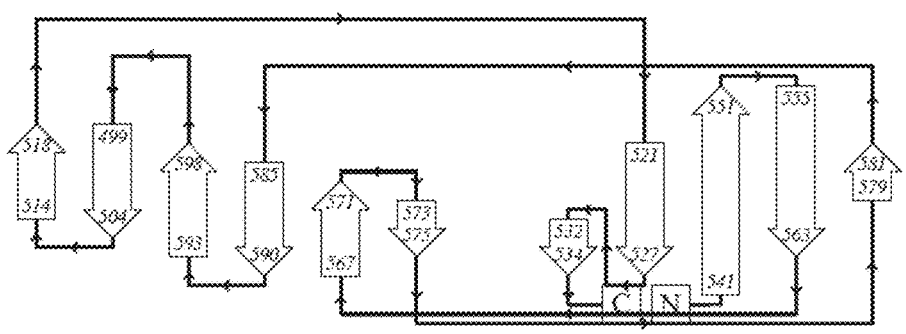

SEQUENCE LISTING

<160> NUMBER OF SEQ ID NOS: 10

<210> SEQ ID NO 1
<211> LENGTH: 7935
<212> TYPE: DNA
<213> ORGANISM: Homo sapiens

<400> SEQUENCE: 1

```
ccagctcgcg ctgcccgggc gggcgccggc cgctggcgcc gctactgctg ccgcccccgg      60
ggcgcgagtc cgccgcccgc cgcccgggca cccggcgagg ggcggggggca gctccgaacc     120
ggccccagat ccttcccgct tccgcctcac gcttcccgga aagcttgtcc ctctccgccg     180
agctgctccg ggagccccgc cgcgccgagg gtatctccca gagccccagc tggtgtggcc     240
aggcccagg agtaggatgg ggctcccct acgagggccg gtggcagcca gaactgatac       300
agccccctg gtctggggcc aggacgccag ctgaggaggg caggagtgtc tggagctatg      360
gctggtgcct cggtgaaagt ggcagtgagg gttcggccct ttaacgcccg tgagaccagc     420
caggatgcca agtgtgtggt cagcatgcag ggcaacacca cctccatcat caatcctaaa     480
cagagcaagg atgccccaa aagcttcacc tttgactact cctactggtc acacacttcg      540
acggaggacc cccagtttgc atctcagcag caagtgtatc gggacattgg agaagagatg     600
ctgctccacg cctttgaagg ctacaacgtg tgcatctttg cctatgggca gaccggggct     660
gggaaatcct ataccatgat ggggcgacag gagccagggc agcagggcat cgtgccccag    720
ctctgtgagg acctcttctc tcgcgttagt gagaaccaga gtgctcagct atcctactct    780
gtggaggtga gctatatgga gatctactgt gagcgggtac gagacctctt gaaccccaag    840
agtcggggtt ctctgcgggt ccgggagcac cccatcctgg gcccgtacgt gcaggacctg    900
tccaaattgg ctgtgacctc ctacgcagac attgctgacc tcatggactg tggaaataaa    960
gcacggactg tggctgccac caacatgaat gagaccagca gccgttccca tgccgtcttt   1020
accatcgtct tcacacagcg ctgccatgac cagctcacgg ggctggactc ggagaaggtc   1080
agtaagatca gtttggtgga ccttgctggg agtgagcgag ccgactcctc aggggcccgg   1140
ggcatgcgcc tgaaggaagg agccaacatc aataagtccc tgactacact agggaaagtg   1200
atctcggccc ttgcagatat gcaatcaaag aagcgaaagt cggattttat cccctacagg   1260
gactctgtgc tcacctggct gctcaaggaa aatttggggg ggaactcacg cacagccatg   1320
attgcagccc tgagccctgc tgacatcaat tacgaggaga ctctcagcac cctcaggtat   1380
gctgaccgca ccaagcaaat ccgctgcaat gccatcatca acgaggaccc taatgcccgg   1440
ctgattagag agctgcagga ggaagtagcc cggctgcggg aactgctgat ggctcaggga   1500
ctgtcagcct ctgctctgga aggcctgaag acggaagaag ggagtgtcag aggcgccctg   1560
ccagctgtgt catctccccc agctccagtt tcaccctcat cacccaccac acataatggg   1620
gagctggagc cgtcattctc ccccaacacg gagtcccaga ttgggcctga ggaagccatg   1680
gagaggctgc aggagacaga gaagattata gctgagctga acgagacatg ggaggagaag   1740
ctacgcaaga cagaagccct gaggatggag agagaagcat tgctggctga gatggggtg   1800
```

```
gccgtccggg aggatggggg aactgtgggc gtcttctctc caaagaagac tccccacctg    1860
gtgaacctga acgaagaccc tctgatgtct gagtgtctgc tctaccacat caaagatggc    1920
gtcaccaggg tcggccaagt agatatggac atcaagctga ccggacagtt cattcgggag    1980
caacactgtc tgttccggag catcccccag ccagatggag aagtggtggt cactctggag    2040
ccttgtgaag gagctgagac atatgtgaat gggaagcttg tgacggagcc gctggtgctg    2100
aagtcaggga ataggattgt gatgggcaag aaccacgttt tccgcttcaa ccacccggag    2160
caggcaaggc tggaacggga acgaggggtc cccccacccc caggaccgcc ctctgagcca    2220
gtcgactgga actttgccca gaaggaactg ctggagcagc aaggcatcga cataaagctg    2280
gaaatggaga agaggctgca ggatctggag aatcagtacc ggaaagaaaa ggaagaagcc    2340
gatcttctgc tggagcagca gcgactgtat gcagactcgg acagcgggga tgactctgac    2400
aagcgctctt gtgaagagag ctggaggctc atctcctcct tgcgggagca gctgccgccc    2460
accacggtcc agaccattgt caaacgctgt ggtctgccca gcagtggcaa gcgcagggcc    2520
cctcgcaggg tttatcagat cccccagcga cgcaggctgc agggcaaaga cccccgctgg    2580
gccaccatgg ctgacctgaa gatgcaggcg gtgaaggaga tctgctacga ggtgggcctg    2640
gctgacttcc gccacgggcg ggctgagatt gaggccctgg ccgccctcaa gatgcggagc    2700
ctgtgtcgca cctatggcaa gccagacggc cccggagacg cctggagggc tgtggcccgg    2760
gatgtctggg acactgtagg cgaggaggaa ggaggtggac ctggcagtgg tggtggcagt    2820
gaggagggag cccgaggggc ggaggtggag gacctccggg cccacatcga caagctgacg    2880
gggattctgc aggaggtgaa gctgcagaac agcagcaagg accgggagct gcaggccctg    2940
cgggaccgca tgctccgcat ggagagggtc atcccctggc ccaggatca tgaggatgag    3000 aatgaagaag gtggtgaggt cccctgggcc ccgcctgaag gatcagaggc agcagaggag    3060
gcagccccca gtgaccgcat gccgtcagcc cggcccccct cgccaccact gtcaagctgg    3120
gagcgggtgt cacggctcat ggaggaggac cctgccttcc gtcgtggtcg tcttcgctgg    3180
ctcaagcagg agcagctacg gctgcaggga ctgcagggct ctggggccg gggcgggggg    3240 ctgcgcaggc ccccagcccg ctttgtgccc cctcacgact gcaagctacg cttcccttc    3300 aagagcaacc cccagcaccg ggagtcttgg ccagggatgg ggagcgggga ggctccaact    3360
ccgctccaac cccctgagga ggtcactccc catccagcca cccctgcccg ccggcctccg    3420
agtccccgaa ggtcccacca tccccgcagg aactccctgg atggaggggg ccgatcccgg    3480
ggagcgggtt ctgcacagcc tgaacccag cacttccagc ccaaaaagca caactcttat    3540
ccccagccac cccaacccta cccagcccag cggcccccag gccccgcta ccccccatac    3600 actactcccc cacgaatgag acggcagcgt tctgcccctg acctcaagga gagtgggca    3660 gctgtgtgag tcccacatcc tgggcagagg gcctggtggg gccccttgct aggagaaggg    3720
aagacgcccg agacgctgct tccccagaag tgctggggca gggaggccca ggagatgaga    3780
gagaaggtcc gagtaggtga tagaagacaa ggggagacc gagccggagg ctgaggaaag    3840
gaagagggca cggagttgcc aggagcaaac caaagtgaag agagagatag gaagctgcct    3900
cggggccacc ccttgcaaag ggggtgtgtc ccacaaacgc tgctatggt ggggtggggg    3960 gctggggtgc tgcgtagcca gtgtttgact ttcttttcaa gtgggggaaa gtgggagagg    4020
actgagagtg aggcaagttc tccccagccc ctgtccgtct gtctgtctgt ctgtggtggt    4080
ttctgtttct tgggaggcat ggtaggatca taagtcattc ccctccccct tccaggcctcc    4140 tgctatattt gggggaccct actggtttgg ctggagtccc atgaggatgt gggccctta    4200
```

```
ataaaggata gcaaacaggg agcttgtggc ctgtttgttt tgggttttca tggaggtgta   4260
ggttatataa ggcaatggca caggtcttaa gcatacttat cagtgaagta ttgtatgtgt   4320
gctctgtgca ggcaccaccc agatctggat ataagaatgt ttccatcttg tcttcctgaa   4380
cttcaccctc ctgtctcttc cttcagggtg cgcagcccga tctttttcccc gctttttttt   4440 tttgggagac agggtcttgc tttgttgccc aggctggagg tacagtcttg gctcactgca   4500
gcctccgcct cctgagtagc tgggattaca ggcatgtgcc accacgcccg gctcattact   4560
gttttttttg tagtgacgag gtttcaccat attggccagg ctggtctcga actcctgatg   4620
acctcaagtg atccgcccac cttggcctcc caaagtggtg ggattacagg tgtgagccac   4680
cgcgcccggc ctcccctgct ttcatgtttg cttacccagt gtctcagtct gtgccagcag   4740
caccactgtc tgttatggac aaagcacaga agcggggatg cgaggggagg tagagggacc   4800
gccagcctgt caatgcttaa ctggctgttg ctgacagata cagaaggatt tgtggggtac   4860
agaggagttc tgctttaagt cacctaactt acttgaaagg tctcccaagc agccagtttc   4920
tcttgatagt gaatgggttg ggcaagcata ctgcgcttac ctgattgttt tcatcctggt   4980
tgtgttacct gccttctggc aggctacatc attgttccca gtcgttattt tatttgtgtt   5040
aagactgttt gttggccagg cgcagtggtt cacgcctgta atgccagcac tgggaggccg   5100
aggcaggtgg atcacgaggt caggagatcg agaccatcct ggctatcatg gtgaaacccc   5160
atctctacta aaaataaaaa taaaaaaatt agccgggcat ggtggcgggg gcctgtagtc   5220
ccagctactc aggaggctga ggcaggagaa tggcatgaac ctgggaggcg gagcttgcag   5280
tgagctgaga ttgcgccact gcactccagc ctgggcgaca gagcgagact ccatttcaag   5340
aaaaattaaa aaactgtttg ttgcctgctt gttttaatgt tctggcttga ggcagcgagc   5400
ccttgactat gccacattgc caggattttg caggttagat tgtactacag cactgccttt   5460
ggcttgccag actctggagt ccccacattt tcatcctgtt ctcaggaaaa cactttgacc   5520
cacttgaagc tctgagctac tgcttcacag cttcctgggg tcagtctcca gccaaaacca   5580
tagatatccc aactgcagcc aaaccacggc tctgggcgaa ggaacgatta ggtttactct   5640
aggtttccac accctgatgc tcctgccttt actttgacac ctctgactgc caggttttca   5700
cagacctgtt gacagtgact caagatctgg aatgtaatgg atggtttggc aacagtgttt   5760
gcttgagcag tttaaaatct ggccagggag actcaatgtg agcaagaaaa tgatagaata   5820
ccaagttttc tggaggtcag agggagctga gttgagtgtt accgagaatg ctgtggggtt   5880
tgagatgaga aaaatagctt gctaatttaa aagacggatt attttttccct aaagaccttg   5940 acttatgtaa atgtatatta tccataattt taaaaatcca cttatggctg ggcacagaag   6000
ctcacacctg taatcccagc actttgggag gctgaggcag gaggatcagt tgagtccagg   6060
agttcgagac cagcctgggc aacatagtga aaccctgtat ctacaaaaca tagaaaaact   6120
agttgggtgt ggtggtgtgt acctgtagtt ccagctacta gggaggtagg aagatcacct   6180
gagcccatgg agattgaggc tgtggtgagc tgtgaaggca ccacagcact ctggcctggg   6240
caagagtggg actctctcaa aaaaaaaaaa aaaaaaaaat ccacatatcc agccttccaa   6300
gtcagtcttt aataatgtgc acgggccagg cacagtggct cacacccgta atcccaacac   6360
tttggaatat tagggtggga gcatcacttg aggccaggaa tttgagacca gcctgggcaa   6420
catagtgaga ctgccccccc catctctaca aaaataaaaa atcaaaaata atactgtggg   6480
caaactttac ttagatttta ttcagagtag tgcctgtttta ttttcatct gtgctacctg   6540
```

```
tgccggcatt ccatatgcat ttgatttagt ctttaaagta ccccggtaaa ataggtcttt      6600
tgtctgcatt tttcagatgg gaagactgag gttttgttta tttattttta tttatttatt      6660
ttttgagacg gagtctcgct ctgttgccta ggctggagtg cgatggcaca atcttggctc      6720
actacaacct ccgcttcctg ggttcaagcg attctcctgc ctcagcctcc tgagtagcta      6780
ggattacagg cgcccacaac cgcacccggc taatttttg tatctttagt agagacaggg      6840
tttcactatg ttgtccaagc tggtttcgaa ttcctgacct caggtgatcc acccgcctct      6900
gcctcccaaa atgttgggat tacaggcgtg agccaccacg cccagcctat ttatttattt      6960
ttttagaatc aagatcttgc tatgttgccc aggctgaact cgaactcctg ggctcaagca      7020
atcctgcctc ccaagccaag cagctggtac tgcaagcatg tgccaccgtg cctggctcct      7080
gaagactgag gttggtttag attaatgagt tgcccaaatt cagacagttc ttaagtggca      7140
aagttaggat tccaacccag gtcaacataa ctaaagccca aaccccatct caccccctcta     7200 ggccatcaag tattggctgg gtgcggtggt ttatgtctgt aatcccagca ctttgggagg      7260
cggaggcggg aggactgttt gagctcagga gtttgagacc agcctgggca ataacaag       7320 accctgtctc tacaaaaata tataaattag ccgggtgtac tggctcacac ctgtagctac      7380
ttgggaggct gaggtgggag gatcgcttga gcctgggagg tcaaggctgc ggtgacctgt      7440
gattgcacca ccaggagacc ctgtcttaaa aatgtatata taaaataaa aagaacatca       7500 gacatcacca tcacctcgct tagaatccat ggggccttct cctcaaattc aatcttccca      7560
ggcatttcat gaacttgcgt ctagtttctg ttccctctca aattgcccag gctgtcctgt      7620
gagtgacagc agctatttcg tgggcctcct ctggaatcat gagaagtcac ccaaacaatc      7680
tcagttttct agctcactcc gtcttgacat ttctacactg tcatccttgg ttttcttgga      7740
aattaatttg cttttcttca ttgtctttct ttggagctgc tttccttttg ttggttacta      7800
ttttattttt agcttctcac accataccga catatgttgg ttattctttt agacatgttt      7860
tttgttgttg ttgtcacctg gaacttttgt atcttgaata aatttgggga tcaaataaaa      7920
aaaaaaaaaa aaaaa                                                        7935

<210> SEQ ID NO 2
<211> LENGTH: 350
<212> TYPE: DNA
<213> ORGANISM: artificial sequence
<220> FEATURE:
<223> OTHER INFORMATION: Circular permutant of the 2G1L FHA domain

<400> SEQUENCE: 2
aaatttacca tgggcctgat gagcgaatgt ctgctgtatc atattaaaga tggtgttacc       60
cgtgttggtc aggtggatat ggatattaaa ctgacaggcc agtttattcg tgaacagcat      120
tgtctgtttc gtagcattcc gcagccggat ggtgaagttg ttgttaccct ggaaccgtgt      180
gaaggtgcag aaacctatgt taatggtaaa ctggttaccg aaccgctggt tctgaaaagc      240
ggtaatcgta ttgttatggg caaaaaccat gtgtttcgct taatcatac cggcaccggt      300 agcacaccgc atctggttaa tctgaatgaa gatccggcgg ccgcaattaa                 350

<210> SEQ ID NO 3
<211> LENGTH: 350
<212> TYPE: DNA
<213> ORGANISM: artificial sequence
<220> FEATURE:
<223> OTHER INFORMATION: Circular Permutant of 2G1L

<400> SEQUENCE: 3
```

```
aaatttacca tgggcgcaga aacctatgtg aatggtaaac tggttaccga accgctggtt      60
ctgaaaagcg gtaatcgtat tgttatgggc aaaaaccatg tgtttcgctt taatcatacc     120
ggcaccggta gcacaccgca tctggttaat ctgaatgaag atccgctgat gagcgaatgt     180
ctgctgtatc atattaaaga tggtgttacc cgtgttggtc aggtggatat ggatattaaa     240
ctgacaggcc agtttattcg tgaacagcat tgtctgtttc gtagcattcc gcagccggat     300
ggtgaagttg ttgttaccct ggaaccgtgt gaaggtgcgg ccgcaattaa                350
```

<210> SEQ ID NO 4
<211> LENGTH: 350
<212> TYPE: DNA
<213> ORGANISM: artificial sequence
<220> FEATURE:
<223> OTHER INFORMATION: Circular permutant of 2G1L

<400> SEQUENCE: 4

```
aaatttacca tggcattcg tgaacagcat tgtctgtttc gtagcattcc gcagccggat       60
ggtgaagttg ttgttaccct ggaaccgtgt gaaggtgcag aaacctatgt taatggtaaa     120
ctggttaccg aaccgctggt tctgaaaagc ggtaatcgta ttgttatggg caaaaaccat     180
gtgtttcgct taatcatac cggcaccggt agcacaccgc atctggttaa tctgaatgaa     240
gatccgctga tgagcgaatg tctgctgtat catattaaag atggtgttac ccgtgttggt     300
caggtggata tggatattaa actgacaggc cagtttgcgg ccgcaattaa                350
```

<210> SEQ ID NO 5
<211> LENGTH: 57
<212> TYPE: DNA
<213> ORGANISM: artificial sequence
<220> FEATURE:
<223> OTHER INFORMATION: Mutagenesis primer of 2G1L and circular
      permutants of 2G1L
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t

<400> SEQUENCE: 5

```
ggttccaggg taacaacasn nsnnsnnsnn snnsnnsnna tgctacgaaa cagacaa        57
```

<210> SEQ ID NO 6
<211> LENGTH: 51

-continued

```
<212> TYPE: DNA
<213> ORGANISM: artificial sequence
<220> FEATURE:
<223> OTHER INFORMATION: Mutagenesis primer for 2G1L and circular
      permutant of 2G1L
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t

<400> SEQUENCE: 6
accagatgcg gtgtgctasn nsnnsnnsnn snntgattaa agcgaaacac a            51

<210> SEQ ID NO 7
<211> LENGTH: 102
<212> TYPE: PRT
<213> ORGANISM: homo sapien

<400> SEQUENCE: 7

Thr Pro His Leu Val Asn Leu Asn Glu Asp Pro Leu Met Ser Glu Cys
1               5                   10                  15

Leu Leu Tyr His Ile Lys Asp Gly Val Thr Arg Val Gly Gln Val Asp
                20                  25                  30

Met Asp Ile Lys Leu Thr Gly Gln Phe Ile Arg Glu Gln His Cys Leu
            35                  40                  45

Phe Arg Ser Ile Pro Gln Pro Asp Gly Glu Val Val Thr Leu Glu
        50                  55                  60

Pro Cys Glu Gly Ala Glu Thr Tyr Val Asn Gly Lys Leu Val Thr Glu
65                  70                  75                  80

Pro Leu Val Leu Lys Ser Gly Asn Arg Ile Val Met Gly Lys Asn His
                85                  90                  95

Val Phe Arg Phe Asn His
            100

<210> SEQ ID NO 8
<211> LENGTH: 107
<212> TYPE: PRT
<213> ORGANISM: artificial sequence
<220> FEATURE:
<223> OTHER INFORMATION: Circular permutation of 2G1L

<400> SEQUENCE: 8

Leu Met Ser Glu Cys Leu Leu Tyr His Ile Lys Asp Gly Val Thr Arg
1               5                   10                  15

Val Gly Gln Val Asp Met Asp Ile Lys Leu Thr Gly Gln Phe Ile Arg
                20                  25                  30

Glu Gln His Cys Leu Phe Arg Ser Ile Pro Gln Pro Asp Gly Glu Val
            35                  40                  45

Val Val Thr Leu Glu Pro Cys Glu Gly Ala Glu Thr Tyr Val Asn Gly
```

```
           50                 55                 60
Lys Leu Val Thr Glu Pro Leu Val Leu Lys Ser Gly Asn Arg Ile Val
 65                 70                 75                 80

Met Gly Lys Asn His Val Phe Arg Phe Asn His Thr Gly Thr Gly Ser
                 85                 90                 95

Thr Pro His Leu Val Asn Leu Asn Glu Asp Pro
            100                 105

<210> SEQ ID NO 9
<211> LENGTH: 107
<212> TYPE: PRT
<213> ORGANISM: artificial sequence
<220> FEATURE:
<223> OTHER INFORMATION: Circular permutation of 2G1L

<400> SEQUENCE: 9

Ala Glu Thr Tyr Val Asn Gly Lys Leu Val Thr Glu Pro Leu Val Leu
 1               5                  10                 15

Lys Ser Gly Asn Arg Ile Val Met Gly Lys Asn His Val Phe Arg Phe
                20                 25                 30

Asn His Thr Gly Thr Gly Ser Thr Pro His Leu Val Asn Leu Asn Glu
                35                 40                 45

Asp Pro Leu Met Ser Glu Cys Leu Leu Tyr His Ile Lys Asp Gly Val
    50                 55                 60

Thr Arg Val Gly Gln Val Asp Met Asp Ile Lys Leu Thr Gly Gln Phe
 65                 70                 75                 80

Ile Arg Glu Gln His Cys Leu Phe Arg Ser Ile Pro Gln Pro Asp Gly
                85                 90                 95

Glu Val Val Val Thr Leu Glu Pro Cys Glu Gly
                100                105

<210> SEQ ID NO 10
<211> LENGTH: 107
<212> TYPE: PRT
<213> ORGANISM: Artificial Sequence
<220> FEATURE:
<223> OTHER INFORMATION: Circular Permutant of 2G1L

<400> SEQUENCE: 10

Ile Arg Glu Gln His Cys Leu Phe Arg Ser Ile Pro Gln Pro Asp Gly
 1               5                  10                 15

Glu Val Val Val Thr Leu Glu Pro Cys Glu Gly Ala Glu Thr Tyr Val
                20                 25                 30

Asn Gly Lys Leu Val Thr Glu Pro Leu Val Leu Lys Ser Gly Asn Arg
                35                 40                 45

Ile Val Met Gly Lys Asn His Val Phe Arg Phe Asn His Thr Gly Thr
    50                 55                 60

Gly Ser Thr Pro His Leu Val Asn Leu Asn Glu Asp Pro Leu Met Ser
 65                 70                 75                 80

Glu Cys Leu Leu Tyr His Ile Lys Asp Gly Val Thr Arg Val Gly Gln
                85                 90                 95

Val Asp Met Asp Ile Lys Leu Thr Gly Gln Phe
                100                105
```

ENGINEERED FHA DOMAINS

FIELD OF THE INVENTION

The present invention relates to engineering non-endogenous forkhead-associated (FHA) domains having substantially the same conserved beta-sheet scaffold but, through circular permutation, the polypeptide presents a novel sequence between one or more of the beta strands. The engineered FHA domain may be randomized to construct libraries which may be screened for novel binding interactions with various target molecules/antigens. The engineered FHA domain variants binding affinity may involve the randomization of the loops of the endogenous binding face of the FHA domain and/or the randomization of the loops located on the opposite to the endogenous binding face of the FHA domain.

This application claims the benefit of priority of the provisional application 62/327,422 filed on Apr. 25, 2016, and incorporates by reference the U.S. patent application Ser. No. 14/497,320 filed on Sep. 25, 2014.

BACKGROUND OF THE INVENTION

FHA is structurally conserved in both Prokarya and Eukarya, featuring a β-sandwich architecture generally comprised of a 5-strand β-sheet and an opposing 6-strand β-sheet. Endogenous proteins having an FHA domain are associated with binding to phosphothreonine moieties and phosphotyrosine. This interaction is mediated by a protein sequence displayed on a common face of the FHA domain, produced by the protruding loops that facilitate the connectivity of various β-sheet strands.

This arrangement of a structurally conserved core, with an interaction specific variable loop region make the FHA domain an effective antibody-like protein (ALP). By generating DNA libraries that encode for randomized variable loop regions of an FHA domain while maintaining the integrity of the conserved core scaffold, established display techniques can be employed to generate an FHA domain to specifically interact with practically any desired target. Such a capability has intracellular and extracellular implications, both, as a research tool and as a therapeutic tool.

The expression of a protein library using an endogenous protein framework having an FHA domain may be more taxing on the cell due to endogenous sequences that may not be essential for the FHA scaffold and/or target binding. Furthermore, such use may result in lower yield of expression of the recombined protein. The use of the endogenous protein framework may also not be optimal for the required thermo-stability, binding affinity to a desired target binding, or other types of activity. There may be other issues such as solubility or a higher risk of proteolytic degradation. The endogenous structure may also limit the use of adding additional domains for binding to other targets, markers, or biocatalysts.

INVENTION SUMMARY

The invention is an engineered FHA domain comprised of a rearranged primary amino acid sequence, which may be characteristic of circular permutation, where the naturally occurring sequences of the protein may be rearranged, added, deleted, or removed such that the resulting primary amino acid sequence still structurally folds in to a functional FHA domain. The engineered FHA domain proteins may be used to generate a library of randomized variants for the purposes of selecting a particular variant that binds to a desired target.

In one embodiment of the engineered FHA domain, the original amino- and carboxy- (N- and C-, respectively) terminal ends of the domain may be strategically engineered so that the resulting primary amino acid sequence still structurally folds as a FHA, through with the N- and C-termini arranged elsewhere in the domain, compared to wild type (WT). Extra protein sequence(s) of varying length may be introduced to join the former N- and C-termini. The extra protein addition may also introduce a new loop into the face of the FHA domain, opposite the endogenous binding interface. This allows for a completely new binding interface or opposite binding interface to be engineered, which may be created through a randomized DNA library of at least the location of the newly formed loop. As a result, a bi-specific FHA scaffold may be created such that the engineered FHA domain binds to one molecule/target through the typical endogenous binding interface and binds to a second, separate molecule/target via the newly introduced opposite binding interface, where the N- and C-termini previously were found. The engineered FHA domain may also include introducing multiple newly formed loops that do not interfere with the stability of the FHA scaffold, and may be further randomized in creating a variant library.

By placing the newly introduced N- and C-termini where a loop of the conserved binding face previously occupied, characterized peptides of known interactions can be introduced and thus present with a free end on the endogenous binding face. Distinct peptide sequences can be introduced at each terminus so that the resulting interface displays two separate binding motifs. In combination with the introduced opposite binding interface of the engineered FHA, the inclusion of additional peptide sequences added to the termini may result in a tri-specific FHA: one domain binding to three different molecules/targets.

Targets/molecules of the newly engineered FHA protein may include a peptide or polypeptide, nucleic acids, ions/radioisotopes.

The variant engineered FHA domain containing may include proteins having multiple copies of FHA. Some FHA domains that are known to form homodimers may be also be used to create a randomized library for circular permutants.

The present invention may also include a kit for generating high affinity engineered FHA proteins. The kit may include the necessary oligonucleotides for randomizing the newly engineered loop or loops as well as the conserved loops between the sequences of the conserved beta-sheet scaffold of the engineered FHA display vector. The display vector may be suitable for either phage-display libraries or ribosome-display libraries. The kit may further include, but is not limited to the necessary reagents for primer extension and ligation.

The synthesis of an engineered protein that binds to a desired target molecule may be used for a variety of preparative, analytical, diagnostic or therapeutic purposes.

BRIEF DESCRIPTION OF THE DRAWINGS

FIG. 1 is of schematic representations of the wild type FHA domain and the exemplary embodiments of the engineered FHA protein scaffolds.

FIG. 2A is an exemplary SDS-PAGE gel image of Ni-NTA purified peak fractions from the recombinant protein expressions of each engineered FHA protein of FIG. 1.

SEQUENCE LISTINGS

Figure 2A:
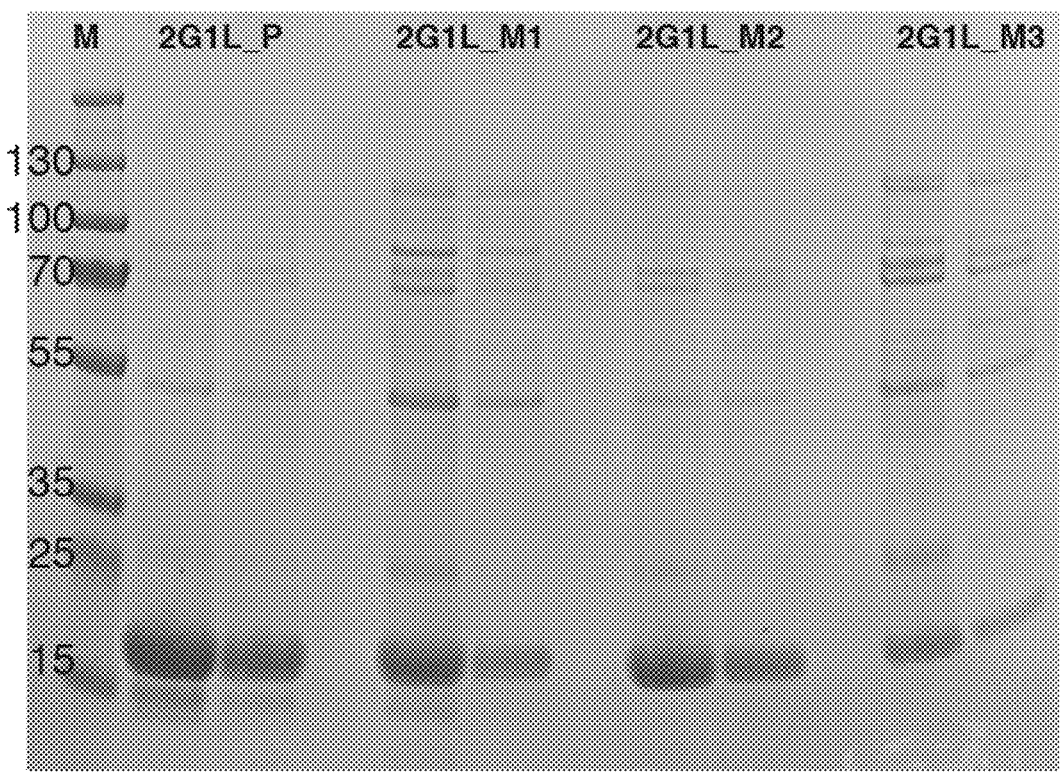
FIG. 2B is an exemplary overlay of SEC profiles Ni-NTA purified peak fractions from the recombinant protein expressions of each engineered FHA protein of FIG. 1.

The sequence listing nucleic and amino acids are provided using standard letter abbreviations for nucleotide bases, and three letter code for amino acids, as defined in 37 C.F.R. 1.822. Only one strand of each nucleic acid sequence is shown as it is understood in the art as to the sequence of the complementary strand of the displayed strand. The Sequence Listing is submitted as an ASCII text file in the form of the file named Sequence_listing.txt (~18 kb), which was created on Apr. 25, 2017 and is incorporated by reference herein.

DETAILED DESCRIPTION OF DRAWINGS

Definitions

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A laboratory Manual, $4^{th}$ edition (2012) Cold Spring Harbor Laboratory Press, Cold Spring Harbor, N.Y. and Current Protocols in Molecular Biology (Ausbel et al., eds., John Wiley & Sons, Inc. 2001. As appropriate, procedures involving the use of commercially available kits and reagents are generally carried out in accordance with manufacturer defined protocols and/or parameters unless otherwise noted.

The following definitions, unless otherwise stated, apply to all aspects and embodiments of the present application.

An "oligonucleotide" refers to a single stranded DNA, RNA, or a DNA-RNA hybrid nucleic acid strand that may be approximately 18 to 30 nucleotides in length. Oligonucleotides can hybridize to genetic material such as DNA, cDNA, or mRNA. Oligonucleotides can be labeled at their 5'-terminus via an amino- or thiol-linker or at the 3'-terminus via an amino link with, but not limited to, fluorophores such as Cy3™, Cy5™, fluorescein, quenchers such as Dabcyl or T-Dabsyl, or alternative labels such as biotin and radioisotopes. Labeled oligonucleotides may function as probes to detect the presence of nucleic acids with a complementary nucleic acid sequence. Labeled or unlabeled oligonucleotides may also be used as primers necessary for performing PCR when cloning or detecting the presence of a gene. Oligonucleotides are prepared synthetically by solid-phase synthesis using modified or unmodified 2'-deoxynucleosides (dA, dC, dG, and dT) or ribonucleosides (A, C, G, U).

The terms "protein", "peptide", and "polypeptide" refer to a linear macromolecular polymer of at least two natural or non-natural amino acids covalently linked together by peptide bonds. A protein, peptide, or polypeptide has a free amino group at the N-terminus and a free carboxyl group at the C-terminus unless circular or specifically tagged at the N- or C-terminus. The amino acid sequence of a protein, peptide, or a polypeptide is determined by the nucleotide sequence of a gene. Proteins, peptides and polypeptides may have a primary, secondary, and tertiary structure. At times, the protein, peptide, or polypeptide may also be post-translationally modified with prosthetic groups or cofactors.

A "plasmid" is a vector that refers to an independently replicating circular double-stranded piece of DNA. The plasmid may contain an origin of replication such as the *E. coli* oriC, an selectable antibiotic resistance gene conferring resistance to but not limited to β-lactam, macrolide, and aminoglycosides antibiotics, a promoter sequence under expression control, and a multiple cloning site containing restriction sites which may or may not contain a coding sequence for an antibody like protein described herein.

The plasmid may be an "expression plasmid" or "expression vector." Expression plasmids allow for the expression of a cloned gene. An expression plasmid contains an inducible promoter region that allows for the regulation and induction of gene expression of a gene cloned into the plasmid's multiple cloning site, a ribosomal binding site, a start codon, a stop codon, and a termination of transcription sequence.

The term "recombinant protein" refers to a protein that is expressed from an engineered "recombinant DNA" coding sequence. Recombinant DNA combines at least two separate DNA strands into one strand that would not have been normally made in nature. Molecular cloning is used to construct recombinant DNA and may involve the amplification of a DNA fragment of interest and then inserting the fragment into a cloning vector. The recombinant DNA is then introduced into a host organism which is then screened and selected for the presence of the inserted recombinant DNA.

The term "protein expression" refers to the production of protein within a host cell such as a bacterium, yeast, plant, or animal cell. A vector carrying the coding sequence for a recombinant protein under the control of a promoter, such as an expression plasmid, is inserted into a host cell. The promoter controlling the expression of the recombinant gene is then induced and the protein encoded by the recombinant gene is produced within the host cell.

The term "protein purification" refers to a process of purifying a protein and may employ any technique used to separate and isolate a protein of interest to a satisfactory level of purity. Protein purification exploits a protein's various properties such as size, charge, binding affinity, and biological activity. Liquid column chromatography is commonly used in protein purification where a cell lysate containing an expressed protein is passed over a "resin" with particular binding affinity for the protein of interest. A resin is a compound or a polymer with chemical properties that supports the purification of proteins via ion exchange, hydrophobic interaction, size exclusion, reverse phase, or affinity tag chromatography. A protein may also be purified by non-chromatographic techniques such as through the electroporation of protein from an excised piece of a polyacrylamide gel that contained a protein sample of interest.

A "protein tag" refers to an amino acid sequence within a recombinant protein that provides new characteristics to the recombinant protein that assist in protein purification, identification, or activity based on the tag's characteristics and affinity. A protein tag may provide a novel enzymatic property to the recombinant protein such as a biotin tag, or a tag may provide a means of protein identification such as with fluorescence tags encoding for green fluorescent protein or red fluorescent protein. Protein tags may be added onto the N- or C-terminus of a protein. A common protein tag used in protein purification is a poly-His tag where a series of approximately six histidine amino acid residues are added which enables the protein to bind to protein purification matrices chelated to metal ions such as nickel or cobalt. Other tags commonly used in protein purification include chitin binding protein, maltose binding protein, glutathione-S-transferase, and FLAG-tag. Tags such as "epitope tags" may also confer the protein to have an affinity towards an antibody. Common antibody epitope tags include the V5-tag, Myc-tag, and HA-tag.

The terms "fusion protein" or "fused protein" refer to a protein that is coded by a single gene and the single gene is made up of coding sequences that originally coded for at least two or more separate proteins. A fusion protein may retain the functional domains of the two or more separate proteins. Part of the coding sequence for a fusion protein may code for an epitope tag. As described herein for the antibody like protein, a fusion protein may also contain sequences that code for a variety of proteins having varying functional roles based on its application.

The term "protein coding sequence" refers to a portion of a gene that codes for a polypeptide. The coding sequence is located between an ATG initiation of translation codon and the location of a TAG, TAA, or TGA termination of translation codon. Typical to eukaryotic genes, the coding sequence may include the "exons" of a gene, which is the sequence of a gene that is transcribed and translated into a polypeptide, and may exclude the "introns" of a gene, which is the sequence of a gene that is transcribed but not translated into a polypeptide.

The term "transformation" refers to a process of introducing exogenous genetic material into a bacterium by methods employing membrane permeability via chemical or electrical means. Performing a transformation involves adding genetic material, such as a plasmid, to an aliquot of competent bacterial cells, such as *E. coli*, and allowing the mixture to incubate on ice. The bacterial cells are then either electroporated or placed at 42° C. for approximately 1 minute and then returned to incubate on ice. The bacterial cells are then grown on an agar plate overnight until colonies are visible. The agar plate may contain antibiotic or nutrient conditions for colony selection.

The term "transfection" refers is the process of deliberately introducing nucleic acids into cells. The term is often used for non-viral methods in eukaryotic cells. It may also refer to other methods and cell types, although other terms are preferred: "transformation" is more often used to describe non-viral DNA transfer in bacteria, non-animal eukaryotic cells, including plant cells. In animal cells, transfection is the preferred term as transformation is also used to refer to progression to a cancerous state (carcinogenesis) in these cells. "Transduction" is often used to describe virus-mediated DNA transfer. *Nature Methods* 2, 875-883 (2005).

The term "circular permutation" refers to the number of ways to arrange a protein's amino acid peptide sequence such that the protein structure has different connectivity, but in some cases, the "circular permutant" may have a similar three-dimensional (3D) shape or core structure to the wild type sequence. Generally, the N- and C-termini are joined together directly or indirectly, and a new N- and C-termini are created between two adjacent beta strand structural elements. Additional sequences that may include cloning sites can be included as well as Circular permutation may be determined through artificial engineering of mutations. Various algorithms may be used to engineer possible viable circular permutations.

The terms "phage display" and "phage library" refer to a defined and well known technique used for the display and production of polypeptides on the surface of a phage virus as first described by Smith G P. Sci. 228(4705):1315-7 (1985). Among the polypeptides that can be displayed on the surface of a phage library are antibodies and antibody fragments such as Fab and scFVs as described by McCafferty et. al. Nat. 348(6301):552-554 (1990), Barbas et. al. Proc. Natl. Acad. Sci. 88(18):7978-82 (1991), Burton et. al. Proc. Natl. Acad. Sci. 88(22): 10134-7 (1991), Barbas et. al. Proc. Natl. Acad. Sci. 89(10):4457-61 (1992), and Gao et. al. Proc. Natl. Acad. Sci. 96(11): 6025-30 (1999). In a phage display, non-essential genes of a bacteriophage are removed and a unique gene of interest in the form of cDNA, herein the cDNA encoding for the antibody like protein, is inserted into the phage gene sequence encoding the phage surface protein of a phage display vector. Bacteria such as *E. coli* are transformed with the phage display vector as well as infected with a helper phage enabling for the expression and packaging of the relevant cDNA encoding a polypeptide product, such as the engineered FHA domain containing proteins described herein, on the bacteriophage surface. A library of phage with the displayed randomized protein can then be screened and selected for by binding to a specific target or molecule of interest. Target molecule of interest may also be referred to as an antigen. Antigens may range from any molecule including the general biochemical classes of nucleic acids, lipids and fats, proteins, and sugars. Once a phage that exhibits binding to a target has been identified, the phage can then be isolated and used for a second round of infection and screening. Multiple rounds of screening and selection can be performed to identify the polypeptide having the desired target binding affinity.

The term "ribosome display" refers to a technique that is used to identify and evolve a select protein that binds to a specific target. In a ribosome display, DNA from an oligonucleotide library is inserted and ligated into a ribosome display vector. The inserted gene of interest is then amplified via PCR. In vitro transcription transcribes the amplified PCR product into mRNA which is then translated in vitro. The mRNA-ribosome-polypeptide complex is then used for affinity assays by binding the complex to an immobilized target. Non-binding mRNA-ribosome-polypeptide complexes are removed by washing and the target bound mRNA-ribosome-polypeptide complex is recovered. The mRNA from the recovered mRNA-ribosome-polypeptide complex may be amplified by PCR and the display selection process may then be repeated to enrich for a gene product with enhanced target specificity. Random mutations may be introduced after each round of selection to further enrich for a gene product with enhanced target specificity.

The term "CIS display" refers to a technique that enables the display and selection of peptides and proteins from extremely large libraries through the use of in vitro display technology. In vitro transcription is initiated at the promoter and pauses when the RNA polymerase reaches the CIS element. Concurrent translation produces the target protein, which transiently interacts with the CIS element, thereby forcing its subsequent binding to the adjacent peptide sequence. This process establishes a faithful linkage between a template DNA and the expressed polypeptide that it encodes.

The term "mutagenesis" may refer to any type of process or method well known in the art used to make alterations to the genetic information of an organism. It may occur spontaneously in nature or via mutagens or experimentally using laboratory techniques. Some exemplary methods may include site-directed mutagenesis, Kunkel's mutagenesis, cassette mutagenesis, whole plasmid mutagenesis, and in vivo site-directed mutagenesis.

The term "Kunkel's mutagenesis" refers to a method traditionally practiced by inserting the DNA fragment to be mutated into a phagemid and then transforming it into a bacteria cell line that is deficient in dUTPase and uracil deglycosidase such that ssDNA having dUTP serves as template for mutagenesis. (Kunkel Proc. Nat. Acad. Sci. 82(2): 488-92 (1985). Following mutagenesis of the extract ssDNA, the parent ssDNA and the mutated DNA are transformed into a bacterial cell line not having a deficiency of dUTPase and uracil deglycosidase and in which case the uracil containing parent DNA strand, and not the mutated strand, is ultimately degraded. Some exemplary methods are provided by the following references: Fellouse, et al. J. Mol. Biol. 373(4): 924-940 (2007) and Tonikian, et al. Nat. Protoc. 2(6): 1368-1386 (2007).

The term "MAX randomization" is a process of non-degenerate saturation mutagenesis using exactly 20 codons (one for each amino acid) or else any required subset of those codons. The randomization saturates codons located in isolated positions within a protein or on one face of an alpha-helix. The process involves cloning solely the codons that collectively represent the favored codon for expression of each amino acid. It may be used to quickly construct overlapping gene libraries through the use of zinc finger proteins. Furthermore, the randomization helps eliminate redundant codons both to minimize gene library size and to eliminate inherent amino acid bias. In addition, this process also eliminates termination codons at randomized positions.

The term "polyclonal" refers to produced by, involving, or being derived from two or more cells of different ancestry or genetic constitution.

The term "monoclonal" refers to produced by, involving, or being derived from a single cell line.

The term "phage selection" refers to the method that identifies variants within a bacteriophage library that binds to the targeted antigen. One method involves the use of ELISA where plates are coated with primary antibody proteins and probed with a bank of bacteriophages displaying different peptides or polypeptides at its surface. The phage-peptides that bind to primary antibodies are detected by a secondary antibody coupled with an enzyme with quantifiable activity. An exemplary enzyme may be horseradish peroxidase (HRP).

A "therapeutic molecule" refers to a chemical compound that provides a medicinal purpose. Therapeutic molecules may be any drug, anesthetic, vitamin or supplement known in the art, and may be listed in the Orange Book of Approved Drug Products with therapeutic Equivalence Evaluations provided by the U.S. Food and Drug Administration (www.accessdata.fda.gov) or any chemical, drug, or biological molecule listed in the Merck Index (www.rsc.org/merck-index).

The term "conserved sequence" refers to a sequence of nucleotides in DNA or RNA, or amino acids in a polypeptide, that are similar across a range of species. Conserved sequences are represented by a nucleotide or an amino acid that occurs at the highest frequency at a particular site in a homologous gene or protein from the same or different species. The term "non-conserved sequence" refers to a sequence of nucleotides or amino acids in a gene or protein that are not conserved and that have a higher variability than conserved sequences.

The term "Zimm plot" refers to the plot used to determine the molecular weight and relative Rayleigh ratio and dRI. These values are determined using the expression:

$$\frac{K^*c}{R(\theta, c)} = \frac{1}{M_W P\theta} + 2A_2 c$$

Where $R(\theta, c)$ is the excess Rayleigh ratio of the solution as a function of scattering angle $\theta$ and concentration $\chi$. It is directly proportional to the intensity of the scattered light in excess of the light scattered by the pure solvent. c is the solute concentration. $M_w$ is the weight-averaged solute molar mass. $A_2$ is the second virial coefficient in the virial expansion of the osmotic pressure. $K^*$ is the constant $4\pi^2(dn/dc)^2 n_0^2/N_a \lambda_0^4$. $N_a$ is Avogadro's number. This number always appears when concentration is measured in g/mL and molar mass in g/mol. $P(\theta)$ describes the angular dependence of the scattered light, and can be related to the rms radius. See also http://www.wyatt.com/library/theory/multi-angle-light-scattering-theory.html.

Circular Permutation of the FHA Domain

Structural rearrangement of the FHA domain may be generated through circular permutation, which is known to occur in some cases, naturally while some may be generated artificially. This bioengineering technique may also employ the use of predictive software for fold recognition in developing the rearranged structure without disrupting the conserved FHA beta sheet scaffold. An example of predictive software is Phyre 2. (http://www.sbg.bio.ic.ac.uk/phyre2/html/page.cgi?id=index.)

One aspect of the invention is to create a binding interface on a circular permutant FHA domain that is novel or non-endogenous from the conserved FHA domain. An exemplary embodiment of the invention may be a circular permutant having additional peptide sequences between joined former amino and carboxy terminal ends. Such a circular permutant may be used to create a DNA library encoding the where the additional peptide sequences are randomized, and variants are then selected for binding affinity properties in the newly created binding interface. Such a binding interface may be located in a region that is opposite of the endogenous binding interface.

FIG. 1B-1D are schematic representations of exemplary engineered FHA protein scaffolds which are circular permutants of the derived from the FHA domain human kinesin family member C, parent 2G1L, ("P"; SEQ ID 7) (as shown in FIG. 1A and derived from the KIF1C gene (SEQ ID 1). The P sequence was visualized using Chimera (https://www.cgl.ucsf.edu/chimera/) for designing the circular permutants. The circular permutants were then evaluated using Phyre 2. Optimized gene blocks were determined using Genart's online tool (https://www.thermofisher.com/us/en/home/life-science/cloning/gene-synthesis/geneart-gene-synthesis.html).

Each of the circular permutants shows possible rearrangements where the original amino- and carboxy-termini ends are joined by an added linker, and new amino- and carboxy-termini ends are created between or around the conserved scaffolds. The linker may be any sequence that preferably increases the thermo-stability of the scaffold and/or does not substantially interfere with the folding of the FHA scaffold, or increases the thermostability of the scaffold. Each schematic representation uses the wild type amino acid numeration of the 5-strand β-sheet and opposing 6-strand β-sheet forming the structurally conserved FHA domain β-sandwich.

The additional protein sequence that is introduced to join the former N- and C-termini may be of varying length. The additional sequence may be used to form a new loop into the face of the circular permutant FHA domain that is opposite of the conserved binding face. Each of the examples in FIG. 1B-1D, the added peptide linker sequence is TGTGS. This allows for the generation of a new and non-endogenous binding interface. One possible method in developing a novel binding interface is to construct variants through selection from a randomized DNA library that encodes for circular permutant FHA domain variants with the newly added loop having a mutation, addition, insertion, replacement or deletion of the sequence. These selected variants may have an FHA scaffold that has two binding interfaces. The selected variants may also be considered to be bispecific where the scaffold is capable of binding one molecule/target through the typical endogenous binding interface and a second, separate molecule/target via the introduced opposite binding interface where the N- and C-termini previously were found.

Insertions of known, not necessarily randomized peptides or polypeptides may also be added to the newly added loop of a circular permutant FHA domain. The peptides or polypeptides may have a domain or domains with known interactions and/or well-characterized functional roles. Such domains may include, but are not limited to fluorescent protein domain or a T4 lyzozyme domain in place of the added loop.

Circular permutants capable of binding to a target molecule may be generated using FHA domains with binding interactions with non-endogenous targets engineered at the endogenous binding interface. Such FHA domains may be constructed using such methods as described in the U.S. patent application Ser. No. 14/497,320 filed on Sep. 25, 2014.

Additional peptide or polypeptide sequences having known functional activities or binding interactions may be introduced to the newly introduced N- and C-termini of the circular permutant FHA domain. Some embodiments may include the addition of a fused protein. The fused protein may be another type of protein, another particular protein domain, or may another FHA domain containing protein. One possible embodiment may be a protein having three or four different binding specificities where two of the binding interactions are located on the engineered FHA domain as described, and the third and fourth afforded by the protein/peptide sequences fused to one or more termini of the FHA domain. Such introduced peptides or polypeptides may have a known function and/or well-characterized interaction, or of a novel amino sequence identified from a randomized library to bind to a specific protein or other biologically relevant target choice.

Polynucleotides encoding any of the above circular permutants of the FHA domain, may be generated, cloned into any suitable expression vector (e.g., pET, pQE, T7 promoter vectors, etc.), expressed constitutively or transiently in an appropriate host cell (e.g. *E. coli*), and evaluated for proper expression. Multiple copies of the engineered FHA domain may also be inserted into an expression vector such that the expressed protein may have tandem FHA domains or more.

Other Possible FHA Domains

FHA domains are present in more than 200 different proteins with each of these proteins having the highly conserved FHA domain β-sandwich. (Durocher et al. FEBS Letters, 2001) Any of these FHA domains from these different proteins may be used in forming a circular permutant and the circular permutant may be further used to generate a randomized DNA library as discussed above. Some other examples of FHA-containing proteins include, but are not limited to Rad53 (i.e. FHA1 and FHA2), KIF1Bβ, Yhr115c, Nbs1, KAPP, EspA, Dun 1, XRS2, and Fkh2. Other FHA domains include FHA-like domains that do not naturally exist and may have been created based on computational modeling after endogenous FHA domains. In another embodiment, the CC1 domain may be used such that individual FHA domains may form homodimers. (Huo et al., Cell Struc., 20, 1550-1561.)

Phage-Display and Variant Selection

A phage engineered FHA domain library may be generated based on methods described by Schofield et. al., Gen. Bio., 8, (R254)1-18 (2007) or any other methods known in the art. FIG. 4 provides an exemplary diagram of the method for creating the phage library and selecting a variant based on its binding affinity. The randomized engineered FHA domain codons may be inserted into vectors such as the pSANG4. (Id.) The recombinant expression plasmids may be transformed in bacterial cells through electroporation or other equivalent methods. The method requires bacterial cells expressing the F pilus in order for phage to gain entry into the cell. Possible cell lines which typically carry the low copy number F plasmid are preferred and may be, but are not limited to, the K12 derivative line, TG-1 cells. After successful transformation and selection of colonies, expression of the engineered FHA domain variants is carried out under the absence of glucose. In cell lines that have an inducible RNA polymerase gene under the control of a lac promoter, IPTG may be used to induce expression for engineered FHA domain variants.

Further to this exemplary embodiment, the transformed bacterial cells may then be subjected to superinfection in order to produce recombinant phage particles. Helper phage such as M13KO7 or KM13 may be used in the preferential packaging of the phagemid DNA into a phage particle.

In the exemplary embodiment of FIG. 4, library rescue and phage selection may be carried out as described in Vaughn et al., Nat Biotechnol 14(3):309-314, Kristensen and Winter, Fold Des. 3 (5) 321-328, Goletz et al., J. Mol. Biol. 315(5):1087-1097. Binding to a target molecule may be evaluated based on a variety of methods. Such methods may include the use of adding a fused tag to the engineered FHA domain variants prior to constructing the Phage-FHA library or monitoring the binding of the target molecule directly to the engineered FHA domain variant. Analytical methods may include, but are not limited to ELISA, biochemical assay, and cell-based assays.

A method of selection of one or more engineered FHA domain variants that binds to one or more target molecules may also combine the use of ribosome-display with phage display as either a primary or secondary means of selection. (e.g. Pelletier, et al. Nat. Biotechnol. 17:683-690 and WO2015048391A)

Kit

Another aspect of the invention provides kits useful in generating high affinity engineered FHA proteins, supra. Kits of the invention may facilitate the generation of libraries using the various embodiments of the engineered FHA domains. Oligonucleotides that may be used to randomize the loop regions between the sequences that encode for the highly conserved beta-sheet scaffold of the FHA domain may also be included. Various materials and reagents for practicing the assays of the invention may also be provided. Kits may contain reagents including, without limitation, expression vectors, cell transformation or transfection reagents, enzymes, as well as other solutions or buffers useful in carrying out the assays and other methods of the invention. Kits may also include control samples, materials useful in calibrating the assays of the invention, and containers, tubes, microtiter plates and the like in which assay reactions may be conducted. Kits may be packaged in containers, which may comprise compartments for receiving the contents of the kits, instructions for conducting the assays, etc.

EXAMPLE 1

One exemplary circular permutant, 2G1L_M1 ("M1") (SEQ ID 2, SEQ ID 8) was engineered based on the parent FHA domain 2G1L (P) nucleic acid sequence found in the KIF1C gene sequence (SEQ ID 1, SEQ ID 7). The engineered codon optimized gene blocks were subjected to restriction digest of NotI-NcoI (New England Biolabs) and the inserted into the pSANG15 vector (Martin, Rojas et al., BMC Biotechnology, 6: 46, 2006) using standard cloning techniques. Constructs were transformed into E. coli BL21 (DE3) competent cells for recombinant protein expression and sequence confirmation. Cultures were then centrifuged at 4000 g for 15 minutes, and the resuspended pellets were sonicated. The cellular debris was further removed by centrifugation at 4000 g for 30 min, and the lysate was filtered through a 5 μm filter (Sartorius Stedim).

Figure 2B:
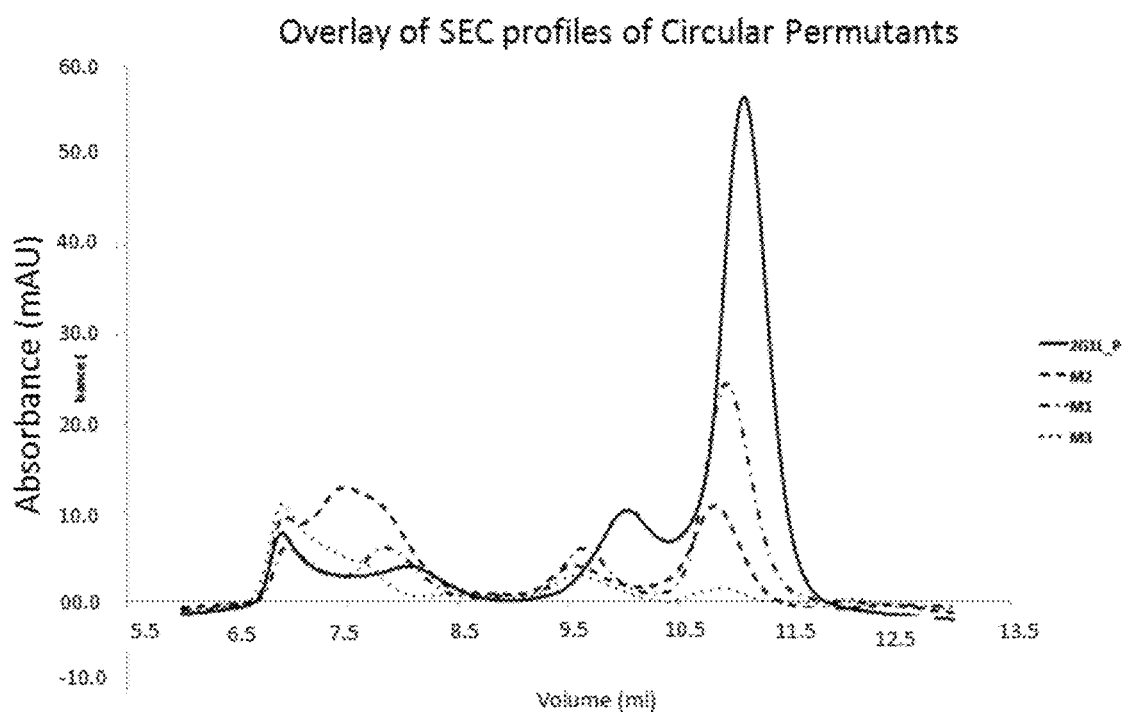
Figure 3A:
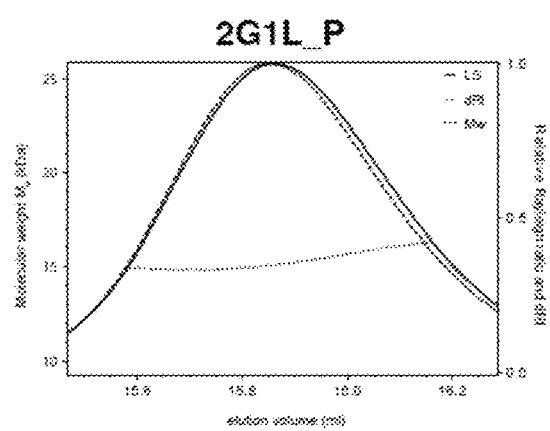
FIG. 3 is an exemplary data of SEC-MAL from each monomeric gel filtration peak of the recombinant protein expressions of each engineered FHA protein of FIG. 1.
Figure 3B:
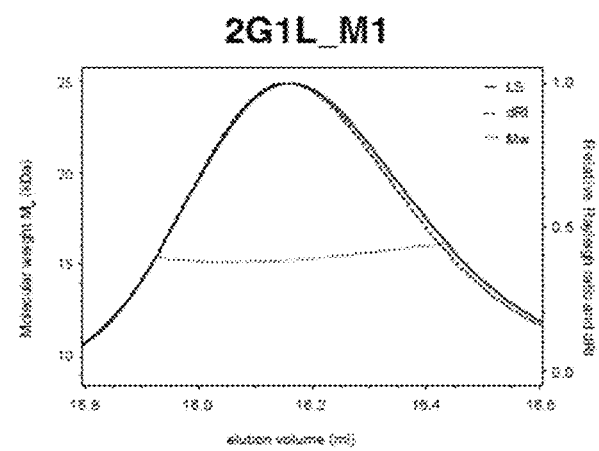
Figure 3C:
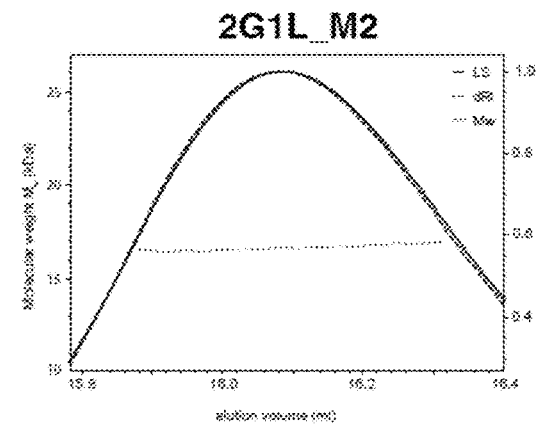
Figure 3D:
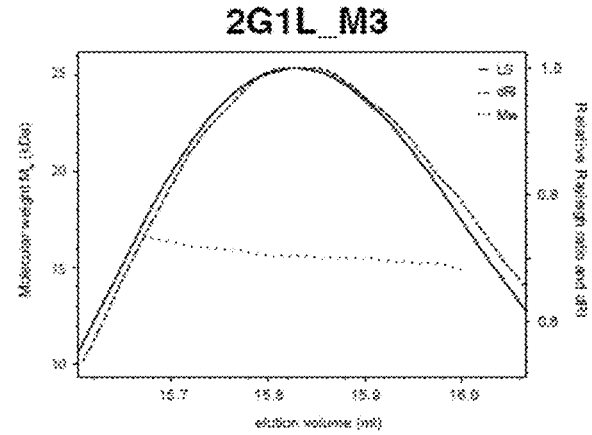
Figure 4:
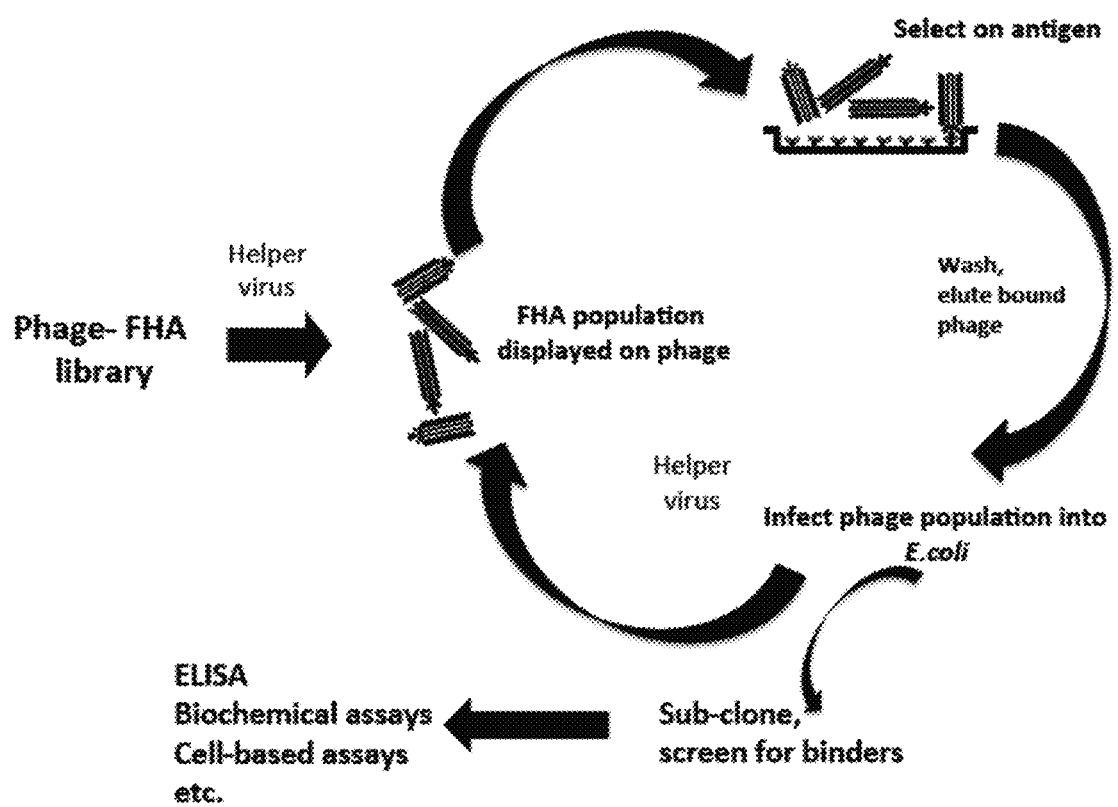
FIG. 4 is a schematic representation of phage display selection.

The lysate was then further separated by Co-NTA affinity chromatography. (Qiagen) The peak fractions were then analyzed by SDS-PAGE. FIG. 2A shows that M1 is soluble and with a yield similar to P. The peak fractions were then concentrated using a 3K molecular weight centrifugal filter (Sartorius Stedim) and applied to a size-exclusion chromatography (SEC) using a Superdex 200 10/300 (GE healthcare). As shown in FIG. 2B, the peak corresponding to correct MW was collected and applied to a size-exclusion chromatography coupled multi-angle lighting scattering column (SEC-MALS) for analytical gel filtration. (Wyatt Dawn Heleos II and Wyatt Optilab T-rED). Samples were resolved on a Superdex 200 Increase 10/300 analytical gel filtration column prior to passing through the light scattering and refractive index detectors. Data was collected and analyzed using ASTRA 6 software (Wyatt Technology). Molecular weights with estimated errors were calculated across each protein peak using Zimm plots with a do/dc value of 0.1850 ml/g. FIG. 3B shows the average monomeric molecular weight of M1 which is similar to that of the average molecular weight of P as shown in FIG. 3A.

The engineered M1 was cloned into the pSANG4 plasmid using the Nco1-Not1 restriction sites. The plasmid was then use for subsequent randomization. Engineered M1 libraries were designed using two oligo-directed Kunkel mutagenesis with the primers SEQ ID 5 and SEQ ID 6 that randomize two loop regions opposite of the. In this exemplary embodiment, titer plates estimated a library size to be $5 \times 10^9$ variants.

Polyclonal library rescue and phage selection were carried out as previously described (Vaughan, Williams et al. 1996, Kristensen and Winter 1998, Goletz, Christensen et al. 2002). One exemplary phage selection was for an engineered FHA domain variant that binds to the target antigen E. coli β-galactosidase to demonstrate the present invention.

Phage displaying engineered FHA were rescued by infecting stocks into TG-1 cells with helper phage at a multiplicity of infection (MOI)=10. Cultures were then centrifuged and the phage supernatant was isolated and concentrated. Phage dilutions of 10×, 1× and 01× were made for each round of selection, and blocked using dried milk in 1×PBS (M-PBS).

ELISA plates were coated with β-galactosidase and blocked with M-PBS. After rounds of washing in PBS, the phage dilutions were then transferred to the appropriate wells of the plates and incubated. Following PBS-Tween washes, the plates were then incubated with mouse anti-M13 antibody and M-PBS. After subsequent washes with PBS-Tween and PBS, Europium labeled anti-mouse antibody and M-PBS were then added and incubated for binding. The plates were again washed in PBS-Tween and PBS. DELFIA enhancement solution was then added. Data was then collected using a plate reader with an excitation at 340 nm and an emission measured at 615 nm.

Figure 5:
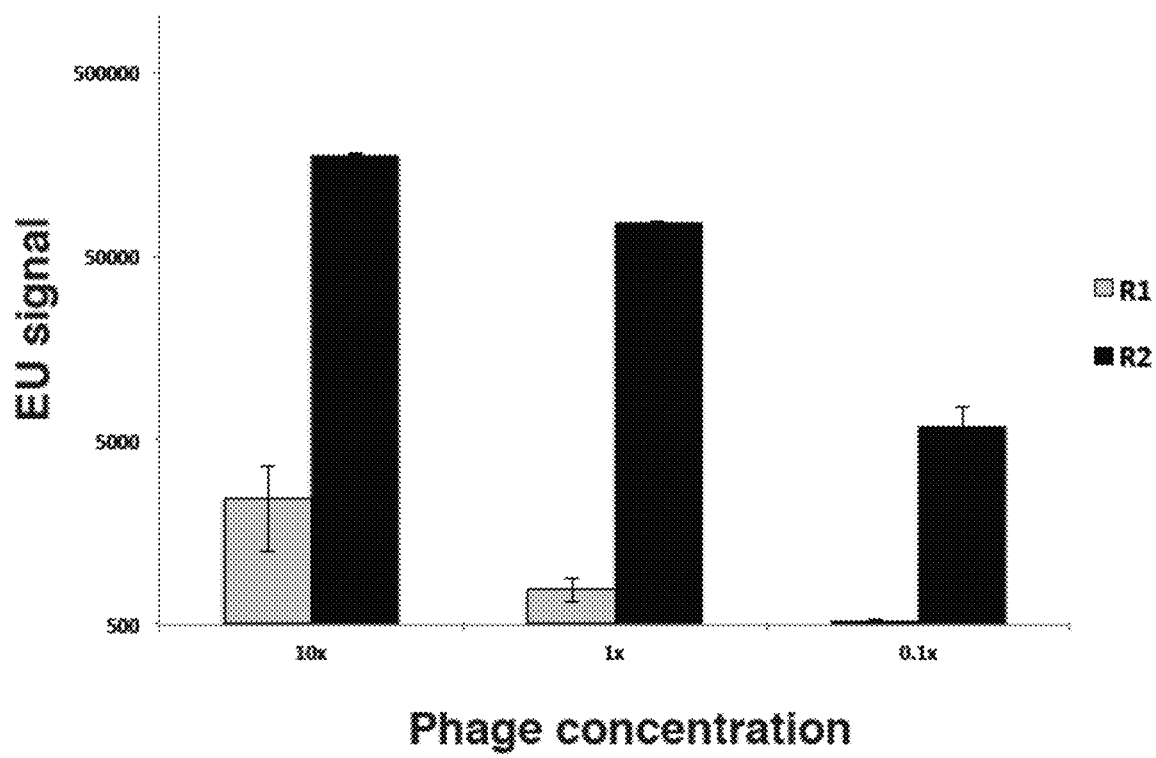
FIG. 5 is an exemplary polyclonal ELISA of *E. coli* β-galactosidase antigen selection.

FIG. 5 shows screens from round 1 (R1) and round 2 (R2) selection of engineered FHA variant of the M1 library which demonstrates that there are variants having affinity binding properties to β-galactosidase.

Prior to screening for individual clones, each selection output was sub-cloned into the expression vector pSANG15 (Supra. Martin, Rojas et al. 2006). FHA gene populations were amplified by PCR from the glycerol stocks of the various selection rounds using primers flanking the FHA domain and subjected to restriction digest with NcoI and NotI (New England Biolabs). The purified amplified DNA was then ligated into NcoI/NotI digested pSANG15 expression vector using T4 DNA ligase (Roche) and then transformed into BL21 (DE3) cells (New England Biolabs).

Figure 6:
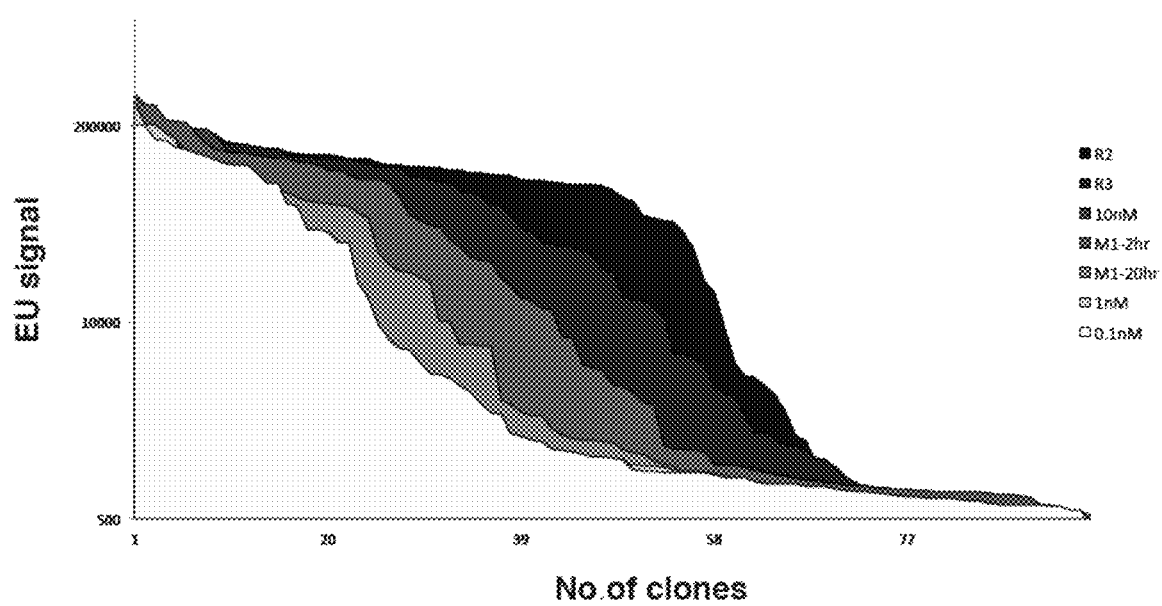
FIG. 6 is an exemplary monoclonal ELISA of *E. coli* β-galactosidase antigen selection.

ELISAs were performed using the procedures described in Martin et al. 2006. Ninety-four (94) clones for each selection campaign were selected, and were grown using auto-induction media. (Studier 2005) Following overnight inductions, bacterial pellets were lysed using Bug Buster (EMD Millipore). Clarified lysates were used in assaying for positive clones and any clones with a specific signal ≥3-fold higher than the control were scored as a positive. FIG. 6 shows M1 variant binding affinity binding to properties to β-galactosidase for the following: round 2 selection ("R2"), round 3 selection ("R3"), bead based selections using limited concentrations of beta-galactosidase from 10 nM, 1 nM, and 0.1 nM, and bead based selections carried out as an "off-rate" selection (i.e. 1-2 h, and 2-20 h) for low dissociating binders.

EXAMPLE 2

FIG. 1C is a topology diagram representation of another embodiment of a circular permutant of the FHA domain protein, 2GIL_M2 ("M2"; SEQ ID: 3, SEQ ID 9), expressed and analyzed similar to Example 1. FIGS. 2A, 2B, and 3 show the expected expression and molecular weights of M2. M2 was randomized using primers SEQ ID 5 and SEQ ID 6. Titer plates estimated a library size of $8 \times 10^9$.

EXAMPLE 3

FIG. 1D is a topology diagram representation of one embodiment of a circular permutant of the FHA domain protein, 2GIL_M3 ("M3"; SEQ ID: 4, SEQ ID 10), expressed and analyzed similar to Example 1. FIGS. 2A, 2B, and 3 show the expected expression and molecular weights of M3.

While the specification describes particular embodiments of the present invention, those of ordinary skill in the art can devise variations of the present invention without departing from the inventive concept.

The invention claimed is:

1. A binding agent that binds to a target molecule comprising:

at least one FHA domain, wherein the at least one FHA domain has been circularly permutated, wherein the at least one FHA domain has an endogenous beta-sheet scaffold of the at wherein the at least one FHA domain has an endogenous binding interface and a second binding interface that is opposite the endogenous binding interface, wherein the second binding interface is a non-endogenous FHA domain sequence, wherein the endogenous binding interface, the second binding interface and the circular permutation comprise an amino acid sequence region, wherein the endogenous binding interface, the second binding interface and the circular permutation amino acid sequence region comprises randomized amino acid sequences, wherein the randomized amino acid sequences do not disrupt the stability of the endogenous beta-sheet scaffold of the at least one FHA domain.

2. The binding agent of claim 1 wherein the binding agent has an additional FHA domain.

3. The binding agent of claim 1 wherein the binding agent comprises a protein tag.

4. The binding agent of claim 1, wherein the binding agent further comprises an additional peptide or polypeptide having a high affinity binding property to a molecule.

5. The additional peptide or polypeptide of claim 4 further comprising a domain with a known function or enzymatic activity.

6. The at least one FHA domain of claim 1 wherein the FHA domain comprises a non-endogenous synthetic sequence derived from a method of computational modeling.

7. The binding agent of claim 1, wherein the randomized amino acid sequences increases the stability of the endogenous beta-sheet scaffold of the at least one FHA domain.

8. A method for producing at least one binding agent that binds to a target molecule comprising:

(a) constructing a library that encodes for proteins, wherein each protein is a binding agent, wherein the binding agent is the binding agent of claim 1, where each of the proteins have at least one FHA domain comprising a circular permutation and where the FHA domain has an endogenous beta-sheet scaffold of the FHA domain, an endogenous binding interface, and an opposite interface, and a randomized sequence of the proteins near and/or part of the beta-sheet scaffold, and the randomized sequence and the circular permutation do not substantially disrupt the beta-sheet scaffold or increases the stability of the beta-sheet scaffold;

(b) expressing the proteins of the library;

(c) screening the library for proteins that bind to the target molecule; and (d) selecting at least one of the screened protein as the binding agent.

9. The method of claim 8 wherein the library comprises a phage-display library or a ribosomal-display library.

10. The method of claim 8 wherein each of the proteins have an additional FHA domain.

11. The method of claim 8 wherein each of the proteins further comprises a protein tag.

12. The method of claim 8 wherein each of the proteins further comprises an additional peptide or polypeptide having a high affinity binding property to a molecule.

13. The additional peptide or polypeptide of claim 12 further comprising a domain with a known function or enzymatic activity.

14. The method of claim 8 wherein the at least one FHA domain comprises a non-endogenous synthetic sequence derived from a method of computational modeling.

* * * * *